(12) United States Patent
Li et al.

(10) Patent No.: US 12,315,600 B2
(45) Date of Patent: May 27, 2025

(54) GENOME-WIDE PREDICTION METHOD BASED ON DEEP LEARNING BY USING GENOME-WIDE DATA AND BIOINFORMATICS FEATURES

(71) Applicants: Institute of Crop Sciences, Chinese Academy of Agricultural Sciences, Beijing (CN); National Nanfan Research Institute (Sanya), Chinese Academy of Agricultural Sciences, Sanya (CN)

(72) Inventors: Huihui Li, Beijing (CN); Yingwei Feng, Beijing (CN); Hao Zhang, Beijing (CN)

(73) Assignees: Institute of Crop Sciences, Chinese Academy of Agricultural Sciences, Beijing (CN); National Nanfan Research Institute (Sanya), Chinese Academy of Agricultural Sciences, Sanya (CN)

( * ) Notice: Subject to any disclaimer, the term of this patent is extended or adjusted under 35 U.S.C. 154(b) by 0 days.

(21) Appl. No.: 18/436,053

(22) Filed: Feb. 8, 2024

(65) Prior Publication Data
US 2025/0104813 A1 Mar. 27, 2025

(30) Foreign Application Priority Data
Sep. 21, 2023 (CN) .......................... 202311218507.X (51) Int. Cl.
*G16B 40/00* (2019.01)
*G16B 20/00* (2019.01)

(52) U.S. Cl.
CPC ............. *G16B 40/00* (2019.02); *G16B 20/00* (2019.02)

(58) Field of Classification Search
None
See application file for complete search history.

(56) References Cited

PUBLICATIONS

CNIPA, Notification of First Office Action for CN202311218507.X, Nov. 1, 2023.
Institute of Crop Science, Chinese Academy of Agricultural Sciences (Applicant), Reply to Notification of First Office Action for CN202311218507.X, w/ (allowed) replacement claims, Nov. 8, 2023.
CNIPA, Notification to grant patent right for invention in CN202311218507.X, Nov. 21, 2023.

*Primary Examiner* — G. Steven Vanni
(74) *Attorney, Agent, or Firm* — Hemisphere Law, PLLC; Zhigang Ma (57) ABSTRACT

Genome-wide data is obtained, and data cleansing, data sparsity processing and bioinformatics feature extraction are performed on the obtained genome-wide data; model construction is performed based on the sparsity-processed genome-wide data and the bioinformatics features to obtain a preliminary hybrid model; model training, regularization, and interpretability enhancement are performed on the preliminary hybrid model to obtain a trained model weight and an interpretability analysis corresponding to the trained model weight; learning and uncertainty estimation are performed based on the trained model weight and to-be-predicted genome-wide data on the hybrid model to obtain an integrated prediction result and uncertainties corresponding to the integrated prediction result; and personalized medical advice and decision assistance are performed based on the integrated prediction result, the interpretability analysis, and the uncertainties corresponding to the integrated prediction result.

6 Claims, 1 Drawing Sheet

GENOME-WIDE PREDICTION METHOD BASED ON DEEP LEARNING BY USING GENOME-WIDE DATA AND BIOINFORMATICS FEATURES

TECHNICAL FIELD

The disclosure relates to the technical field of data processing, particularly to a genome-wide prediction method based on deep learning.

BACKGROUND

Genome-wide association studies (GWAS) have been widely used to identify gene mutations related to various diseases or traits. However, traditional methods in the GWAS mainly rely on statistical methods, but due to their limitations on non-linear and complex interaction relationships, these traditional methods may miss some important genetic signals. In recent years, deep learning has been applied in many fields, such as image recognition and natural language processing, showing an ability to surpass traditional machine learning methods. Therefore, analyzing genome-wide data by using the deep learning is expected to reveal more genetic information.

There are many methods for genome-wide prediction, and "Deep Learning-Based Genome-Wide Prediction Method" proposed by Dong Jing with an application No. CN202310351749.X" mainly includes: applying a deep learning method to an information data processing terminal; and constructing a deep learning algorithm model, and inputting the genome-wide prediction data into the constructed deep learning algorithm model. Specially, the deep learning algorithm model includes: an information filtering module, an information coding module, a gene recombination simulation module, a gene prediction module, and a prediction judgment module; an output terminal of the information filtering module is connected to an input terminal of the information coding module, an output terminal of the information coding module is connected to an input terminal of the gene recombination simulation module, an output terminal of the gene recombination simulation module is connected to an input terminal of the gene prediction module, and an output terminal of the gene prediction module is connected to an input terminal of the prediction judgment module. According to the foregoing disclosure, genome combination prediction ability is improved by means of data processing.

However, the above-mentioned methods exist at least the following technical problems: when the genome-wide prediction is performed, the prediction is not accurate enough and the model is unstable.

SUMMARY

According to an embodiment of the disclosure, a genome-wide prediction method based on deep learning is provided, which solves the technical problems of inaccurate prediction and model instability during the genome-wide prediction existed in the related art, and realizes technical effects of a high-stability model and an accurate prediction result.

The disclosure provides the genome-wide prediction method based on deep learning, and specifically includes the following technical solution.

The genome-wide prediction method based on deep learning includes the following steps:

step 1, obtaining genome-wide data, performing data cleansing on the genome-wide data to obtain cleansed genome-wide data, performing data sparsity processing on the cleansed genome-wide data to obtain sparsity-processed genome-wide data, and extracting bioinformatics features from the sparsity-processed genome-wide data;

step 2, performing model construction based on the sparsity-processed genome-wide data and the bioinformatics features to obtain a hybrid model;

step 3, performing model training, regularization, and interpretability enhancement on the hybrid model to obtain a trained model weight and an interpretability analysis corresponding to the trained model weight;

step 4, performing learning and uncertainty estimation based on the trained model weight and to-be-predicted genome-wide data to obtain an integrated prediction result and uncertainties corresponding to the integrated prediction result; and step 5, performing personalized medical advice and decision assistance based on the integrated prediction result, the interpretability analysis, and the uncertainties corresponding to the integrated prediction result.

In an embodiment, in the step 1, the performing data sparsity processing on the cleansed genome-wide data to obtain sparsity-processed genome-wide data specifically includes: performing dimensionality reduction on the cleansed genome-wide data according to principal component analysis to obtain dimensionality-reduced data.

In an embodiment, in the step 1, the performing data sparsity processing on the cleansed genome-wide data to obtain sparsity-processed genome-wide data further includes: performing random projection based on compressed sensing on the dimensionality-reduced data to obtain random-projected data.

In an embodiment, in the step 1, the performing data sparsity processing on the cleansed genome-wide data to obtain sparsity-processed genome-wide data further includes: coding the random-projected data by using a sparse autoencoder.

In an embodiment, during the model construction, the step 2 further includes: constructing the gene interaction graph G and creating a graph structure for an interaction between the genes, specially including:

step 2.1, data acquisition;
step 2.2, data preprocessing;
step 2.3, constructing the graph structure; and
step 2.4, graph attribute analysis.

In an embodiment, the step 3 further includes: performing the model training by using gradient descent in batch to find an optimal parameter to make the hybrid model have an optimal performance during prediction, thereby obtaining the trained model weight.

In an embodiment, the step 3 further includes: adding a constraint term based on a knowledge graph into the optimal loss function to obtain the trained model weight constrained by the knowledge graph.

In an embodiment, the step 3 further includes: adding a regularization layer after an output of each network layer of the hybrid model to obtain a regularized model weight; and analyzing the regularized model weight by using shapley additive explanations (SHAP) and local interpretable model-agnostic explanations (LIME) to obtain the trained model weight and an importance score or a local interpretation model corresponding to each of the bioinformatics features.

In an embodiment, the performing uncertainty estimation in the step 4 specially includes: converting the trained model weight into a probability distribution, introducing a binary neural network, and evaluating an uncertainty of the trained model weight (also referred as to a first uncertainty of the uncertainties corresponding to the integrated prediction result) by using a weight distribution of the binary neural network; regularizing the prior probability distribution of the trained model weight to prevent the posterior probability distribution from overfitting; and evaluating a second uncertainty of the uncertainties corresponding to the integrated prediction result by using a Monte Carlo method to perform approximate estimation, including: using a matrix decomposition technology.

Beneficial Effects

Multiple technical solutions provided in the above embodiments of the disclosure at least have the following technical effects or advantages.
1. The disclosure utilizes the principal component analysis, the random projection, and the compressed sensing to perform the data sparsity processing, realizing the dimensionality reduction of the genome-wide data while minimizing information loss; and uses the complex mapping matrix and graph theory analysis, which can not only enhance the model interpretability, but also can improve the prediction precision.
2. The disclosure uses a convolutional neural network and long short-term memory networks to process structured data and to capture the local features and the long-term dependency relationships of the genes; combines the graph neural network to make the model better capture the complex interaction relationships of the genes, so that those complex biological processes or diseases related to multi-gene interaction can be more accurately predicted by using the graph neural network based on the interaction relationships of the genes, such as multi-gene genetic diseases or complex phenotypic traits.
3. The disclosure is constrained by the knowledge graph, and the model can be combined with existing biological knowledge for learning, so that the prediction result is more accurate, the reliability of the model is enhanced, the deep learning technology and the bioinformatics knowledge are combined, and the prediction result and the interpretability can be applied to medical diagnosis and treatment, as well as can provide valuable directions and suggestions for biological research, thereby promoting innovation and progress in the field of biomedicine.
4. The disclosure provides a method for researchers and doctors to understand the credibility of the preliminary hybrid model by evaluating the uncertainty of the trained model weight; and performs the uncertainty estimation by using the Monte Carlo method, thereby approximately calculating the output variance of the preliminary hybrid model; provides a rapid uncertainty estimation method, avoiding the complex computation; and utilizes the low-rank matrix decomposition to approximate the weight matrix, so that the uncertainty estimation is possible to be performed within the limited time while retaining most of the original information.
5. The technical solutions according to the disclosure can effectively solve the technical problems of inaccurate prediction and model instability during the genome-wide prediction; the disclosure utilizes the principal component analysis, the random projection, and the compressed sensing to perform the data sparsity processing, realizing the dimensionality reduction of the genome-wide data while minimizing information loss, and uses the complex mapping matrix and graph theory analysis, which can not only enhance the model interpretability, but also can improve the prediction precision; the disclosure uses the convolutional neural network and the long short-term memory networks to process structured data and to capture the local features and the long-term dependency relationships of the genes, combines the graph neural network to make the model better capture the complex interaction relationships of the genes, so that those complex biological processes or diseases related to multi-gene interaction can be more accurately predicted by using the graph neural network based on the interaction relationships of the genes, such as multi-gene genetic diseases or complex phenotypic traits; the disclosure is constrained by the knowledge graph, and the model can be combined with existing biological knowledge for learning, so that the prediction result is more accurate, the reliability of the model is enhanced, the deep learning technology and the bioinformatics knowledge are combined, and the prediction result and the interpretability can be applied to medical diagnosis and treatment, as well as can provide valuable directions and suggestions for biological research, thereby promoting innovation and progress in the field of biomedicine; and the disclosure provides the method for researchers and doctors to understand the credibility of the preliminary hybrid model by evaluating the uncertainty of the trained model weight, performs the uncertainty estimation by using the Monte Carlo method, thereby approximately calculating the output variance of the preliminary hybrid model, provides a rapid uncertainty estimation method, avoiding the complex computation, and utilizes the low-rank matrix decomposition to approximate the weight matrix, so that the uncertainty estimation is possible to be performed within the limited time while retaining most of the original information.

DETAILED DESCRIPTION OF EMBODIMENTS

Figure 1:
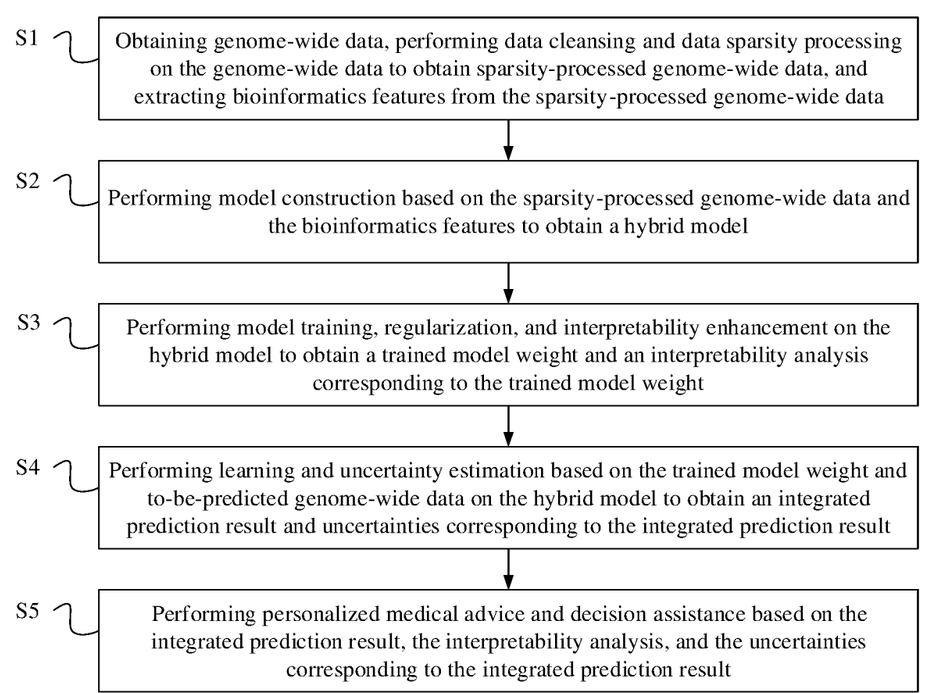
FIGURE illustrates a flowchart of a genome-wide prediction method based on deep learning according to an embodiment of the disclosure.

According to an embodiment of the disclosure, a genome-wide prediction method based on deep learning is provided, which solves the technical problems existed in the related art that prediction is not accurate enough and a model is unstable during the genome-wide prediction. Accordingly, an overall concept of the disclosure is as follows.

Firstly, genome-wide data is obtained, and data cleansing, data sparsity processing and bioinformatics feature extraction are performed on the obtained genome-wide data; model construction is performed based on the sparsity-processed genome-wide data and the bioinformatics features to obtain a preliminary hybrid model; model training, regularization, and interpretability enhancement are performed on the preliminary hybrid model to obtain a trained model weight and an interpretability analysis corresponding to the trained model weight; learning and uncertainty estimation are performed based on the trained model weight and to-be-predicted genome-wide data on the hybrid model to obtain an integrated prediction result and an uncertainty corresponding to the integrated prediction result; and personalized medical advice and decision assistance are performed based on the integrated prediction result, the interpretability analysis, and the uncertainty corresponding to the integrated prediction result, thereby obtaining personalized medical suggestions, gene candidate list of specific disease or trait and medical or biological research direction. Moreover, the disclosure utilizes the principal component analysis, the random projection, and the compressed sensing to perform the data sparsity processing, realizing the dimensionality reduction of the genome-wide data while minimizing information loss, and uses the complex mapping matrix and graph theory analysis, which can not only enhance the model interpretability, but also can improve the prediction precision; the disclosure uses the convolutional neural network and the long short-term memory networks to process structured data and to capture the local features and the long-term dependency relationships of the genes, combines the graph neural network to make the model better capture the complex interaction relationships of the genes, so that those complex biological processes or diseases related to multi-gene interaction can be more accurately predicted by using the graph neural network based on the interaction relationships of the genes, such as multi-gene genetic diseases or complex phenotypic traits; the disclosure is constrained by the knowledge graph, and the model can be combined with existing biological knowledge for learning, so that the prediction result is more accurate, the reliability of the model is enhanced, the deep learning technology and the bioinformatics knowledge are combined, and the prediction result and the interpretability can be applied to medical diagnosis and treatment, as well as can provide valuable directions and suggestions for biological research, thereby promoting innovation and progress in the field of biomedicine; and the disclosure provides the method for researchers and doctors to understand the credibility of the preliminary hybrid model by evaluating the uncertainty of the trained model weight, performs the uncertainty estimation by using the Monte Carlo method, thereby approximately calculating the output variance of the preliminary hybrid model, provides a rapid uncertainty estimation method, avoiding the complex computation, and utilizes the low-rank matrix decomposition to approximate the weight matrix, so that the uncertainty estimation is possible to be performed within the limited time while retaining most of the original information.

In order to better understand the above technical solutions, the above technical solutions are described in detail below with reference to the attached drawing and illustrated embodiments of the disclosure.

With reference to FIGURE, the disclosure provides a genome-wide prediction method based on deep learning and includes the following steps.

Step 1, genome-wide data (also referred as to raw genome-wide data) is obtained, data cleansing is performed on the obtained genome-wide data to obtain cleansed genome-wide data, data sparsity processing is performed on the cleansed genome-wide data to obtain sparsity-processed genome-wide data, and bioinformatics features are extracted from the obtained sparsity-processed genome-wide data.

Firstly, the raw genome-wide data containing a large amount of genotype information is obtained through a next-generation sequencing (NGS) of a laboratory; in order to ensure data quality and improve a training effect of a model (i.e., a preliminary hybrid model), the raw genome-wide data is subjected to the data cleansing, which utilizes quality control software such as PLINK (referred as to whole genome association analysis toolset) or genome analysis toolkit (GATK) to screen the raw genome-wide data, and then to remove genotype data with errors, high deletion rates, or low quality, as well as remove abnormal data points caused by sequencing prejudice, experimental errors, etc., thereby obtaining the cleansed genome-wide data, and then using the obtained cleansed genome-wide data as input data of subsequent steps.

In an illustrated embodiment, in order to reduce dimensionality of the input data and computational complexity, as well as to retain as much useful information as possible, the data sparsity processing is performed on the cleansed genome-wide data, which specially includes the following steps.

Firstly, dimensionality reduction is performed on the cleansed genome-wide data according to principal component analysis to obtain dimensionality-reduced data, and the cleansed genome-wide data is represented by X, each row in which represents a sample, and each column in which represents a gene locus. Specially, a covariance matrix of the X is calculated by the following formula:

$$\sum = \frac{1}{N}\sum_{i=1}^{N}(X_i - \mu)(X_i - \mu)^T.$$

In the above formula, $\Sigma$ represents the covariance matrix of the genome-wide data (i.e., the dimensionality-reduced data), N represents a number of samples, $X_i$ represents an $i^{th}$ sample, and $\mu$ represents an average of the genome-wide data. Moreover, the above formula is used to facilitate understanding correlation between various gene loci, and then eigenvectors and eigenvalues are calculated by the following formula:

$$\sum V = V\Lambda.$$

In the above formula, V is an eigenvector and represents a direction of a principal component; $\Lambda$ is a diagonal matrix; and elements on a diagonal of the diagonal matrix are the eigenvalues and represent an importance of the principal component.

Furthermore, the principal component analysis implements the dimensionality reduction by projecting the raw genome-wide data onto several principal components, which are main variations of the raw genome-wide data, so that the genotype information is lost as little as possible.

Thereafter, first k principal components are determined (according to an empirical method) to obtain the dimensionality-reduced data expressed by a formula as follows:

$$X_{pca} = X \times V_k.$$

In the above formula, $V_k$ represents a matric composed of the first k principal components.

Although the principal component analysis can greatly realize the dimensionality reduction, biologically meaningful information may be lost when processing the raw genome-wide data, and it is possible to perform random projection based on compressed sensing, which is used to calculate the dimensionality-reduced data $X_{pca}$ processed by the principal component analysis as follows:

$$Y = A \times X_{pca}.$$

In the above formula, A represents a random matrix, which comes from certain specific probability distributions, such as Gaussian distribution, and the above formula describes how to perform the random projection by means of the random matrix A to obtain new dimensionality-reduced data Y (i.e., random-projected data).

The random projection based on compressed sensing may retain a structure of the raw genome-wide data in some cases, may further realize the dimensionality reduction while reducing information loss caused by the principal component analysis.

In an illustrated embodiment, the next-generation sequencing may introduce noise, and the noise may interfere with a training process of the deep learning model, resulting in poor performance for the model, so that a sparse autoencoder needs to be introduced for coding the random-projected data.

Specially, the random-projected data Y obtained by performing the random projection is coded by using the following formula:

$$h = f(W_{enc} \times Y + b_{enc}).$$

In the above formula, h represents a coded hidden representation, $f$ represents an activation function (such as rectified linear abbreviated ReLU or Sigmoid), $W_{enc}$ and $b_{enc}$ represent a weight and a bias of the sparse autoencoder, respectively. Specially, initial values of the weight and the bias of the sparse autoencoder are usually randomly allocated, and are updated by means of back propagation and gradient descent in a model training process.

A decoding process of a decoder is as follows:

$$Y' = g(W_{dec} \times h + b_{dec}).$$

In the above formula, Y' represents reconstructed data after the decoding process; g represents another activation function; $W_{dec}$ and $b_{dec}$ represent a weight and a bias of the decoder, respectively. Specially, initial values of the weight and the bias of the decoder are usually randomly allocated, and are updated by back propagation and gradient descent in the model training process.

Based on the above, an optimal loss function is defined by a formula as follows:

$$J(\theta) = \frac{1}{n} \sum_{i=1}^{n} \left( \|Y_i - Y'_i\|^2 + \lambda \|W_{enc}\|_1 + \beta \sum_{j=1}^{s} KL(\rho \| \hat{\rho}_j) \right).$$

In the above formula, $J(\theta)$ represents the optimal loss function and includes a reconstruction error between the random-projected data Y and the reconstructed data Y', an L1 regularization (also referred as to lasso regression) of a weight of the sparse autoencoder, and a kullback-leibler (KL) divergence, and is configured to encourage a sparsity of the weight of the sparse autoencoder; $Y_i$ represents an $i^{th}$ sample of the random-projected data obtained by performing the random projection; $Y'_i$ represents a reconstruction result obtained through coding the $i^{th}$ sample by the sparse autoencoder; n represents a total number of the samples corresponding to the random-projected data; A represents a regularization parameter of the L1 regularization, A is configured to control the sparsity of the weight of the sparse autoencoder, and A is determined artificially and be adjusted based on a verification data set; β represents a control parameter, β is configured to control an influence of the KL divergence on a total loss and encourage activation degrees of hidden units of a hidden layer to be close to a preset sparsity parameter ρ, and β is determined artificially and adjusted based on the verification data set; s represents a number of neurons, and is determined according to model design; p is the preset sparsity parameter, ρ represents an average activation degree of the hidden layer, and ρ is configured to be determined artificially; $\hat{\rho}_j$ represents an average activation degree of a $j^{th}$ hidden unit of the hidden layer, and is calculated according to a model output based on a training data set; $\|W_{enc}\|_1$ is a L1 norm of the $W_{enc}$ and represents a sum of absolute values of elements in the $W_{enc}$; and $KL(\rho\|\hat{\rho}_j)$ represents the KL divergence, is configured to measure a difference or a divergence between two probability distributions, and promote activation sparsity of the hidden layers.

The sparse autoencoder finds a more compact data representation by the coding and decoding processes, goals of which are to reduce the noise and further extract the bioinformatics features, thereby obtaining the reconstructed data Y' output by the sparse autoencoder.

In an illustrated embodiment, by using existing biological knowledge, an interpretability of the model is increased, the prediction precision is improved, and the bioinformatics features are extracted from the sparsity-processed genome-wide data, which specifically includes the following steps.

In order to effectively extract the bioinformatics features from the sparsity-processed genome-wide data Y' (also referred as to the reconstructed data), firstly, a correlation mapping relationship needs to be established, and then a correlation mapping matrix T is defined, and any element in the correlation mapping matrix T is calculated by the following formula:

$$T_{ij} = \sum_{k=1}^{n} \left( w_i^k \times \log(v_j + k) \right) + \int_0^1 e^{-\theta x} \frac{d\phi}{dx} dx.$$

In the above formula, n represents a number of the samples corresponding to the reconstructed data; $w_i^k$ represents the weight of an $i^{th}$ gene in a $k^{th}$ sample, and is derived from the importance of the gene in a preliminary experiment or literature; $v_j$ represents an expression quantity of a $j^{th}$ gene, and is directly obtained by the next-generation sequencing; k represents a relative position index between genes; θ represents a time attenuation parameter, and is estimated from time sequence gene expression data; φ represents a potential energy function of an interaction between the genes, and is derived from a gene interaction database; x represents an independent variable in an interval of [0, 1], and $$\int_0^1 e^{-\theta x} \frac{d\phi}{dx} dx$$

represents a cross-correlation between primary genes. Therefore, the genes can be sorted according to the weights and the expression quantity by means of the correlation mapping matrix T, i.e., the correlation mapping matrix T representing the correlation between the genes and the functions thereof.

In order to extract upstream and downstream relationships and interaction relationships of the genes, graph theory and topological data analysis are introduced to define a gene interaction graph G and a laplacian matrix L of the gene interaction graph G to construct a new feature matrix is constructed, and the new feature matrix is expressed as follows:

$$X = SVD(L) \times \left(\sum_{i=1}^{N} a_i \cdot I_i\right).$$

In the above formula, L represents the laplacian matrix of the gene interaction graph G, is constructed from the gene interaction database or the experimental data, and is obtained from the following formula:

$$L = D - A.$$

In the above formula, D represents a degree matrix, and A represents an adjacency matrix. Moreover, SVD(L) represents a singular value decomposition of the laplacian matrix L of the gene interaction graph G; N represents a number of layers of an interaction matrix $I_i$ of the genes; $a_i$ represents a weight of an interaction intensity between the genes, and is derived from the experimental data, such as a co-immunoprecipitation experiment; li represents the interaction matrix located at different layers, and is provided by a public database such as BioGRID (i.e., a database of protein, genetic and chemical interactions) or STRING (referred as to functional protein association networks). Thereafter, the feature matrix X reflecting the interaction relationships of the genes is obtained.

In order to maintain an original structural performance of an annotation of gene function in the sparsity-processed genome-wide data, a structure-retention mapping matrix is constructed, and the structure-retention mapping matrix is expressed as follows:

$$M = \frac{d}{dt}\left(\int_0^1 p(t) \times (q(t) - \sqrt{r(t)}) dt\right).$$

In the above formula, p(t) represents a changing relationship between an annotation of a gene function and a time t; q(t) represents a biological characteristic of a certain disease caused by a gene under the time t; r(t) represents an uncertainty of the gene function at the time t; and $$\int_0^1 p(t) \times (q(t) - \sqrt{r(t)}) dt$$

represents a formula integration based on the annotation of the gene function and other biological characteristics, as well as considering variability of the genes under the interval of [0, 1]. In addition, the genes are performed by integration (i.e., the formula integration) is configured to obtain a global, integrated description of the gene function and the biological characteristics;

$$\frac{d}{dt}$$

is configured to observe how the description changes over the time t, that is, dynamic changes of the function annotation of the gene and other biological characteristics over the time t, which can better understand behavior of the gene at different time points, and provide more structural information for the correlation mapping of the gene in a low-dimensional space.

The final feature extraction is performed, and the correlation mapping matrix, the feature matrix, and the structure-retention mapping matrix are weighted and merged to obtain the bioinformatics features.

The disclosure utilizes the principal component analysis, the random projection, and the compressed sensing to perform the data sparsity processing, realizing the dimensionality reduction of the raw genome-wide data while minimizing the information loss; and uses the complex mapping matrix and graph theory analysis, which can not only enhance the model interpretability, but also can improve the prediction precision.

Step 2, model construction is performed based on the sparsity-processed genome-wide data and the bioinformatics features to obtain a preliminary hybrid model (also referred as to a hybrid model).

Based on the sparsity-processed genome-wide data and the bioinformatics features, a model that combines the traditional deep learning and the graph neural networks is constructed by using the processed data and considering the interaction relationships between the genes, that is, the preliminary hybrid model.

Firstly, the gene interaction graph G is constructed, creating a graph structure for the interaction between the genes, providing a structural basis for the subsequent graph neural network, and including the following steps.

Step 2.1 of data acquisition, gene interaction data of a related specie is downloaded by accessing the BioGRID database or the STRING database; and a gene interaction data set containing the gene interaction data is expressed as follows:

$$D = \{(g_i, g_j, w_{ij})\}_{i,j=1}^{N}.$$

In the above formula, $g_i$ and $g_j$ represent a gene i and a gene j, respectively, which are gene identifiers extracted from the database; $w_{ij}$ represents an interaction weight or a score between the gene i and the gene j, which can come from the experimental data and reflects intensity or credibility of the interaction between the gene i and the gene j. Thereafter, the gene interaction data set D is obtained; however, the gene interaction data set D is raw data for constructing the gene interaction graph G, and needs to be further cleansed and screened.

Step 2.2 of data preprocessing, the gene interaction data set D is cleansed and screened to ensure that only the interaction relationships with higher quality or higher score are reserved, which is expressed as follows:

$$D' = \{(g_i, g_j) \in D \mid w_{ij} \geq \text{threshold}\}.$$

In the above formula, threshold represents a predefined weight threshold based on expert experience, and is configured to determine a quality standard of the retained interaction relationships of the genes. Thereafter, a screened gene interaction data set D' is obtained, which provides a data basis for constructing the subsequent graph structure.

Step 2.3 of constructing the graph structure, the gene interaction graph G is constructed by using the screened gene interaction data set D', which is expressed as follows:

$$G = G(V, E).$$

In the above formula, V is a vertex set, represents the genes, and is composed of all unique genes in the screened gene interaction data set D'; E is an edge set, represents the interaction relationships of the gens, and is determined by each gene pair $(g_i, g_j)$ in the screened gene interaction data set D'. Thereafter, the gene interaction graph G is obtained, which provides the graph structure based on the interaction relationships of the genes for a subsequent graph neural network algorithm.

Step 2.4 of graph attribute analysis, in view of the gene interaction graph G, a graph analysis tool or a library (such as NetworkX, i.e., a software library for creating, manipulating, and studying graphs and networks) is used to calculate some key attributes in the gene interaction graph G, such as the degree of the node, the diameter of the graph, and the clustering coefficient; a structural attribute report of the gene interaction graph G is obtained; and then the attributes and structural characteristics of the gene interaction graph G are preliminarily understood, thereby providing useful information for designing and analyzing the subsequent graph neural network.

In an illustrated embodiment, the sparsity-processed genome-wide data is processed by a multi layered neural network, i.e., using a convolutional neural network capable of capturing local features) and long short-term memory networks (capable of capturing long-term dependency relationships of the genes); and the gene interaction graph G is processed by the graph neural network, such as a graph convolutional network (GCN), and then outputs of the multi layered neural network and the graph neural network are fused by using a fusion strategy, that is, splicing the outputs of the two networks in their corresponding output dimension, and reserving all the information output from the two networks.

The disclosure uses the traditional deep learning models (i.e., the convolutional neural network and the long short-term memory networks) to process the structured data and to capture the local features and the long-term dependency relationships of the genes; combines the graph neural network to make the model better capture the complex interaction relationships of the genes, so that those complex biological processes or diseases related to multi-gene interaction can be more accurately predicted by using the graph neural network based on the interaction relationships of the genes, such as multi-gene genetic diseases or complex phenotypic traits.

Step 3, model training, regularization, and interpretability enhancement are performed on the preliminary hybrid model to obtain a trained model weight and an interpretability analysis corresponding to the trained model weight.

According to a structure of the network (i.e., the convolutional neural network and the long short-term memory networks), the sparsity-processed genome-wide data is divided into the training data set, the verification data set, and a test data set.

In an illustrated embodiment, the model training is performed by using gradient descent in batch to find an optimal parameter, so that the preliminary hybrid model has an optimal performance during prediction, and the trained model weight subjected to the model training is obtained.

In an illustrated embodiment, in order to guide the preliminary hybrid model to learn the biologically meaningful information, a constraint term based on a knowledge graph is added to the loss function to obtain the trained model weight constrained by the knowledge graph, which is specially realized by the following steps.

Step 3.1 of data analysis of the knowledge graph, all nodes in the knowledge graph are scanned, and each node and its corresponding attribute are recorded; entities of the knowledge graph are recorded, including: recording the entities as a set E, each of the entities being represented by $e_i$ to reflect a gene or a biological entity related to the gene; biological relationships related to the genome-wide data are extracted, including: scanning all edges in the knowledge graph, and recording each of the edges and the entities disposed on two ends of the corresponding edge; and all of the biological relationships are recorded as a set R, each biological relationship in which is represented by $r_{ij}$ to reflect the biological relationship between an entity $e_i$ and an entity $e_j$. Thereafter, the biological relationship set R is obtained; biological relationships related to a to-be-predicted target (also referred as to to-be-predicted genome-wide data) are extracted, specially including: selecting an entity set E' related to the to-be-predicted target from the recorded entity set E; selecting a biological relationship set R' related to the entity set E' from the biological relationship set R, i.e., obtaining the entity set E' and the biological relationship set R' related to the to-be-predicted target.

Step 3.2 of constructing the constraint term, the structured data is output, including: constructing a biological relationship matrix M with a size of |E'|×|E'|, for each biological relationship $r_{ij}$ in the biological relationship set R', a value of an intersection point between a $i^{th}$ row and a $j^{th}$ column of the biological relationship matrix M is set as a positive number to represent an association strength of the two entities (i.e., the entity et and the entity $e_j$). Thereafter, the biological relationship matrix M is obtained.

Step 3.3 of modifying the loss function, the constraint term based on the knowledge graph is fused into the loss function, and the preliminary hybrid model is guided to learn to obtain a loss function fused with the constraint term of the knowledge graph.

Step 3.4 of optimizing the preliminary hybrid model, the preliminary hybrid model is trained by using the loss function fused with the constraint term of the knowledge graph with the gradient descent in batch to obtain a model weight constrained by the knowledge graph.

In an illustrated embodiment, in order to improve a training speed and stability of the preliminary hybrid model, as well as prevent overfitting of the preliminary hybrid model, a regularization layer is added after the output of each network layer to obtain a regularized model weight.

In an illustrated embodiment, in order to provide transparency of model prediction, tools such as shapley additive explanations (SHAP), local interpretable model-agnostic explanations (LIME), etc., are used to analyze the regularized model weight to obtain the trained model weight and an importance score or a local interpretation model corresponding to each bioinformatics feature.

Finally, the verification data set is used to evaluate performance, accuracy, and robustness of the preliminary hybrid model according to the related art, thereby obtaining an evaluation report of accuracy, loss, and other related indexes of the preliminary hybrid model.

The disclosure is constrained by the knowledge graph, and the preliminary hybrid model can be combined with the existing biological knowledge for learning, so that the prediction result is more accurate, the reliability of the preliminary hybrid model is enhanced, the deep learning technology and the bioinformatics knowledge are combined, and the prediction result and the interpretability can be applied to medical diagnosis and treatment, as well as can provide valuable directions and suggestions for biological research, thereby promoting innovation and progress in the field of biomedicine.

Step 4, the preliminary hybrid model is performed by learning and uncertainty estimation based on the trained model weight and the to-be-predicted genome-wide data to obtain an integrated prediction result and uncertainties corresponding to the integrated prediction result.

The to-be-predicted genome-wide data is performed by forward propagation calculation through each layer of the trained preliminary hybrid model to obtain the integrated prediction result.

In order to provide a range for the uncertainties corresponding to the integrated prediction result and help researchers or doctors to better understand the credibility of the trained preliminary hybrid model, and to perform the uncertainty estimation, the disclosure further includes the following steps.

Firstly, the trained model weight is converted into a probability distribution, which is expressed as follows:

$$P(W_{i,j} | D) = \frac{P(D | W_{i,j}) P(W_{i,j})}{P(D)}.$$

In the above formula, $P(W_{i,j}|D)$ represents a posterior probability distribution of the trained model weight between an $i^{th}$ neuron of the neurons and a $j^{th}$ neuron of the neurons under the to-be-predicted genome-wide data D; $P(D|W_{i,j})$ represents a probability corresponding to the to-be-predicted genome-wide data D being observed under the trained model weight; $P(W_{i,j})$ represents a prior probability distribution of the trained model weight between the $i^{th}$ neuron and the $j^{th}$ neuron; and P(D) represents a marginal probability of the to-be-predicted genome-wide data D, and is a constant. Therefore, the trained model weight is now no longer a single value, but the probability distribution representing a confidence or uncertainty of the trained model weight.

In order to evaluate an uncertainty of the trained model weight (also referred as to a first uncertainty of the uncertainties corresponding to the integrated prediction result), a binary neural network is introduced, and the first uncertainty is evaluated by using a weight distribution of the binary neural network (BNN), which is expressed as follows:

$$Y_{sample,k} = \sum_{i=1}^{n} \sum_{j=1}^{m} W_{sample,i,j} X_{i,j,k}.$$

In the above formula, $Y_{sample,k}$ represents an output obtained from a $k^{th}$ sampling of the binary neural network; $W_{sample,i,j}$ represents a sampling result obtained through the $k^{th}$ sampling performed in the posterior probability distribution of the trained model weight between the $i^{th}$ neuron and the $j^{th}$ neuron; and $X_{i,j,k}$ represents a sampling result obtained through the $k^{th}$ sampling of the $i^{th}$ neuron and the $j^{th}$ neuron, which usually has been determined because that input data is determined. In addition, the above formula describes how the BNN outputs the generated uncertainty of the trained model weight.

In an illustrated embodiment, in order to ensure that the posterior probability distribution of the trained model weight between the $i^{th}$ neuron and the $j^{th}$ neuron will not be too concentrated (also referred as to overfitting), the prior probability distribution of the trained model weight between the $i^{th}$ neuron and the $j^{th}$ neuron needs to be regularized by using the following formula:

$$L = L_{original} + \lambda \sum_{i=1}^{n} \sum_{j=1}^{m} \log P(W_{i,j}).$$

In the above formula, $L_{original}$ represents an original loss; $\lambda$ represents a regularization coefficient; and $P(W_{i,j})$ represents the prior probability distribution of the trained model weight between the $i^{th}$ neuron and the $j^{th}$ neuron. Moreover, the regularization ensures that the BNN does not completely trust the training data set, and the priori knowledge is also considered.

However, the above process causes an increase in calculated load, resulting in an overlong computation time.

Therefore, in an illustrated embodiment, a second uncertainty of the uncertainties corresponding to the integrated prediction result is evaluated by using a Monte Carlo method to perform approximate estimation, and specially, a matrix decomposition technology is used to reduce the calculated load. Moreover, the Monte Carlo method is expressed as follows:

$$\text{Var}(Y_k) = \frac{1}{M} \sum_{m=1}^{M} (Y_{sample,k,m} - \mu_k)^2.$$

In the above formula, M represents a total number of times of sampling; $\mu_k$ represents an average output of the M times of sampling; and $Y_{sample,k}$ represents the output obtained from the $k^{th}$ sampling of the binary neural network. Therefore, the above formula describes how to calculate an output variance (i.e., the uncertainty corresponding to the integrated prediction result) from the multiple times of the output sampling generated by the BNN.

In an illustrated embodiment, in order to evaluate the reliable second uncertainty within a limited time, a low-rank matrix decomposition is used to approximate a weight matrix W, which is expressed as follows:

$$W \approx U \sum V^T.$$

In the above formula, U, Σ, $V^T$ represent low-rank approximate representations of the weight matrix W; U represents a left vector matrix, a column vector of the U is an orthogonal basis of the weight matrix W; $\Sigma$ represents a diagonal matrix, elements on a diagonal of the diagonal matrix are singular values and arranged in a descending order, and the singular values are non-zero root-mean-square eigenvalues of the weight matrix W; and $V^T$ represents a transpose matrix of a right vector, a row vector of the $V^T$ is another orthogonal basis of the weight matrix W. Furthermore, the low-rank matrix decomposition realizes the uncertainty estimation with fewer computations, while retaining most of the original information.

The disclosure provides a method for researchers and doctors to understand the credibility of the preliminary hybrid model by evaluating the uncertainty of the trained model weight; and performs the uncertainty estimation by using the Monte Carlo method, thereby approximately calculating the output variance of the preliminary hybrid model; provides a rapid uncertainty estimation method, avoiding the complex computation; and utilizes the low-rank matrix decomposition to approximate the weight matrix, so that the uncertainty estimation is possible to be performed within the limited time while retaining most of the original information.

Step 5, personalized medical advice and decision assistance are performed based on the integrated prediction result, the interpretability analysis, and the uncertainties corresponding to the integrated prediction result, thereby obtaining a gene candidate list corresponding to the specific diseases or traits based on the personalized medical advice, and a medical or biological research direction.

When the personalized medical advice and the decision assistance are performed, firstly, it is a key to provide neat, consistent, and complete data for subsequent analysis. By integrating the model prediction result, the interpretability analysis, and the uncertainty estimation, the data are formatted, which ensures the consistency and accuracy of the data, and provides a solid data basis for the subsequent interpretability analysis and personalized medical advice.

Then, in order to determine the gene strongly related to the specific disease or trait, on the one hand, the gene related to the specific disease or trait is screened out based on the interpretability analysis, and on the other hand, a statistical method, such as a chi-square test or a fisher's exact test, is used to verify the exact association between the genes and diseases. The obtained gene list provides the candidate genes for subsequent personalized medical advice.

On this basis, it is particularly important to extract clinical information of a patient from a medical database or an electronic medical record and integrate the clinical information with the previous candidate genes to construct a comprehensive archive containing the candidate genes and the clinical information, so that the archive not only provides a clinical background for medical advice, but also makes advice more targeted and personalized.

After the comprehensive archive is completed, specific treatment advice can be generated by using an expert system based on the data of the archive. Furthermore, considering the uncertainty of model prediction, a credibility score can be allocated to the advice, which not only provides more accurate and targeted medical advice for doctors or patients, but also increases the proposed credibility.

Finally, in order to make full use of the prediction result of the model to assist doctors or researchers in making decisions, the uncertainty estimation is used as a reference basis for the medical decision. For example, a Bayesian method may be employed to estimate the posterior probability of the medical decision. When the decision is combined with other clinical data, such as imaging and biochemical indicators, the tools or report supporting the decision provides a comprehensive and deep reference for the doctors to help make a more intelligent decision.

In summary, the disclosure provides the genome-wide prediction method based on deep learning.

Based on the technical solutions in the above embodiments, the disclosure at least has the following technical effects or advantages.

1. The disclosure utilizes the principal component analysis, the random projection, and the compressed sensing to perform the data sparsity processing, realizing the dimensionality reduction of the raw genome-wide data while minimizing the information loss; and uses the complex mapping matrix and graph theory analysis, which can not only enhance the interpretability of the model, but also can improve the prediction precision.

2. The disclosure uses a convolutional neural network and long short-term memory networks to process the structured data and to capture the local features and the long-term dependency relationships of the genes; combines the graph neural network to make the model better capture the complex interaction relationships of the genes, so that those complex biological processes or diseases related to multi-gene interaction can be more accurately predicted by using the graph neural network based on the interaction relationships of the genes, such as multi-gene genetic diseases or complex phenotypic traits.

3. The disclosure is constrained by a knowledge graph, and the model can be combined with existing biological knowledge for learning, so that the prediction result is more accurate, the reliability of the model is enhanced, the deep learning technology and the bioinformatics knowledge are combined, and the prediction result and the interpretability can be applied to medical diagnosis and treatment, as well as can provide valuable directions and suggestions for biological research, thereby promoting innovation and progress in the field of biomedicine.

4. The disclosure provides a method for researchers and doctors to understand the credibility of the preliminary hybrid model by evaluating the uncertainty of the trained model weight; and performs the uncertainty estimation by using the Monte Carlo method, thereby approximately calculating the output variance of the preliminary hybrid model; provides a rapid uncertainty estimation method, avoiding the complex computation; and utilizes the low-rank matrix decomposition to approximate the weight matrix, so that the uncertainty estimation is possible to be performed within the limited time while retaining most of the original information.

Effect Investigation

The technical solutions according to the disclosure can effectively solve the technical problems of inaccurate prediction and model instability during the genome-wide prediction. Moreover, the above-mentioned system or method has undergone a series of effect investigation. Therefore, the disclosure utilizes the principal component analysis, the random projection, and the compressed sensing to perform the data sparsity processing, realizing the dimensionality reduction of the genome-wide data while minimizing information loss, and uses the complex mapping matrix and graph theory analysis, which can not only enhance the model interpretability, but also can improve the prediction precision; the disclosure uses the convolutional neural network and the long short-term memory networks to process structured data and to capture the local features and the long-term dependency relationships of the genes, combines the graph neural network to make the model better capture the complex interaction relationships of the genes, so that those complex biological processes or diseases related to multi-gene interaction can be more accurately predicted by using the graph neural network based on the interaction relationships of the genes, such as multi-gene genetic diseases or complex phenotypic traits; the disclosure is constrained by the knowledge graph, and the model can be combined with existing biological knowledge for learning, so that the prediction result is more accurate, the reliability of the model is enhanced, the deep learning technology and the bioinformatics knowledge are combined, and the prediction result and the interpretability can be applied to medical diagnosis and treatment, as well as can provide valuable directions and suggestions for biological research, thereby promoting innovation and progress in the field of biomedicine; and the disclosure provides the method for researchers and doctors to understand the credibility of the preliminary hybrid model by evaluating the uncertainty of the trained model weight, performs the uncertainty estimation by using the Monte Carlo method, thereby approximately calculating the output variance of the preliminary hybrid model, provides a rapid uncertainty estimation method, avoiding the complex computation, and utilizes the low-rank matrix decomposition to approximate the weight matrix, so that the uncertainty estimation is possible to be performed within the limited time while retaining most of the original information.

The disclosure is described with reference to the flowchart and/or the block diagram of the method, the device (system), and the computer program product according to the embodiments of the disclosure. It should be understood that each procedure and/or block in the flowchart and/or the block diagram, and combinations of the procedure and/or the block in the flowchart and/or the block diagram, can be implemented by computer program instructions. These computer program instructions may be provided to a processor of a genetic computer, a specific computer, an embedded processor, or other programmable data processing device to generate a machine such that the instructions executed by the processor of the computer or other programmable data processing device generate the device for implementing the functions specified in one or more procedures of the flowchart and/or one or more blocks of the block diagram.

These computer program instructions may also be loaded onto a computer or other programmable data processing device, and then a series of operational steps are performed on the computer or other programmable device to realize a computer-implemented process, such that the instructions executed on the computer or other programmable device provide steps for implementing the functions specified in one or more procedures of the flowchart and/or one or more blocks of the block diagram.

Although illustrated embodiments of the disclosure have been described, those skilled in the related art can make additional changes and modifications to these embodiments once they know the basic concept. Therefore, the disclosure is intended to be interpreted as including the illustrated embodiments and all variations and modifications falling within the scope of the disclosure.

Apparently, those skilled in the art can make various modifications and variations to the disclosure without departing from the spirit and scope of the disclosure. Thus, if these modifications and variations of the disclosure fall within the scope of the disclosure and an equivalent thereof, the disclosure is also intended to include these modifications and variations.

What is claimed is:

1. A genome-wide prediction method based on deep learning, comprising the following steps:

step 1, obtaining genome-wide data;

performing data cleansing on the genome-wide data to obtain cleansed genome-wide data;

performing data sparsity processing on the cleansed genome-wide data to obtain sparsity-processed genome-wide data, comprising:

performing dimensionality reduction on the cleansed genome-wide data according to principal component analysis to obtain dimensionality-reduced data;

performing random projection based on compressed sensing on the dimensionality-reduced data to obtain random-projected data;

coding the random-projected data by using a sparse autoencoder; and defining an optimal loss function by a formula as follows:

$$J(\theta) = \frac{1}{n}\sum_{i=1}^{n}\left(\|Y_i - Y'_i\|^2 + \lambda\|W_{enc}\|_1 + \beta\sum_{j=1}^{s}KL(\rho\|\hat{\rho}_j)\right),$$

wherein in the formula, $J(\theta)$ represents the optimal loss function and comprises: a reconstruction error, an L1 regularization of a weight of the sparse autoencoder, and a kullback-leibler (KL) divergence; $\|Y_i-Y'_i\|^2$ represents the reconstruction error of the optimal loss function, $\lambda\|W_{enc}\|_1$ represents the L1 regularization of the weight of the sparse autoencoder of the optimal loss function, and $KL(\rho\|\hat{\rho}_j)$ represents the KL divergence of the optimal loss function; n represents a total number of samples corresponding to the random-projected data; $Y_i$ represents an $i^{th}$ sample of the random-projected data obtained by performing the random projection; $Y'_i$ represents a reconstruction result obtained through coding the $i^{th}$ sample by the sparse autoencoder; $\lambda$ represents a regularization parameter of the L1 regularization, $\lambda$ is configured to control a sparsity of the weight of the sparse autoencoder, and $\lambda$ is determined and adjusted based on a verification data set; $W_{enc}$ represents the weight of the sparse autoencoder; $\|W_{enc}\|_1$ is an L1 norm of the $W_{enc}$ and represents a sum of absolute values of elements in the $W_{enc}$; $\beta$ represents a control parameter, $\beta$ is configured to control an influence of the KL divergence on a total loss, and $\beta$ is determined and adjusted based on the verification data set; s represents a number of neurons, and is determined according to model design; $\rho$ is a preset sparsity parameter and represents an average activation degree of a hidden layer; $\hat{\rho}_j$ represents an average activation degree of a $j^{th}$ hidden unit of the hidden layer, and is calculated according to a model output based on a training data set; and KL(ρ∥ρ̂_j) represents the KL divergence, and is configured to measure a difference or a divergence between two probability distributions;

extracting bioinformatics features from the sparsity-processed genome-wide data, comprising:

defining a correlation mapping matrix;

introducing graph theory and topological data analysis into the correlation mapping matrix, and defining a gene interaction graph G and a laplacian matrix L of the gene interaction graph G to thereby construct a feature matrix expressed by the following formula:

$$X = SVD(L) \times \left(\sum_{i=1}^{N} a_i \cdot I_i\right),$$

wherein in the formula, SVD(L) represents a singular value decomposition of the laplacian matrix L of the gene interaction graph G; N represents a layer number of an interaction matrix $I_i$; $a_i$ represents a weight of an interaction intensity, and is derived from experimental data of an experiment including a co-immunoprecipitation experiment; $I_i$ represents the interaction matrix located at different layers; and X represents the feature matrix reflecting interaction relationships of genes; and constructing a structure-retention mapping matrix, which is expressed by the following formula:

$$M = \frac{d}{dt}\left(\int_0^1 p(t) \times (q(t) - \sqrt{r(t)})dt\right),$$

wherein in the formula, p(t) represents a changing relationship between an annotation of a gene function and a time t; q(t) represents a biological characteristic of a disease caused by a gene under the time t; and r(t) represents an uncertainty of the gene function at the time t;

step 2, performing model construction based on the sparsity-processed genome-wide data and the bioinformatics features to obtain a hybrid model;

step 3, performing model training, regularization, and interpretability enhancement on the hybrid model to obtain a trained model weight and an interpretability analysis corresponding to the trained model weight;

step 4, performing learning and uncertainty estimation based on the trained model weight and to-be-predicted genome-wide data on the hybrid model to obtain an integrated prediction result and uncertainties corresponding to the integrated prediction result;

wherein the performing uncertainty estimation specifically comprises:

converting the trained model weight into a probability distribution, which is expressed as follows:

$$P(W_{i,j} \mid D) = \frac{P(D \mid W_{i,j})P(W_{i,j})}{P(D)},$$

wherein in the formula, $P(W_{i,j} \mid D)$ represents a posterior probability distribution of the trained model weight between an $i^{th}$ neuron of the neurons and a $j^{th}$ neuron of the neurons under the to-be-predicted genome-wide data D; $P(D \mid W_{i,j})$ represents a probability corresponding to the to-be-predicted genome-wide data D being observed under the trained model weight; $P(W_{i,j})$ represents a prior probability distribution of the trained model weight between the $i^{th}$ neuron and the $j^{th}$ neuron; and P(D) represents a marginal probability of the to-be-predicted genome-wide data D, and is a constant;

introducing a binary neural network, and evaluating a first uncertainty of the uncertainties corresponding to the integrated prediction result by using a weight distribution of the binary neural network, which is expressed as follows:

$$Y_{sample,k} = \sum_{i=1}^{n}\sum_{j=1}^{m} W_{sample,i,j} X_{i,j,k},$$

wherein in the formula, $Y_{sample,k}$ represents an output obtained from a $k^{th}$ sampling of the binary neural network; $W_{sample,i,j}$ represents a sampling result obtained through the $k^{th}$ sampling performed in the posterior probability distribution of the trained model weight between the $i^{th}$ neuron and the $j^{th}$ neuron; n represents the total number of samples corresponding to the random-projected data; m represents a total number of the bioinformatics features; and $X_{i,j,k}$ represents a sampling result obtained through the $k^{th}$ sampling of the $i^{th}$ neuron and the $j^{th}$ neuron;

regularizing the prior probability distribution of the trained model weight between the $i^{th}$ neuron and the $j^{th}$ neuron, which is expressed by the following formula:

$$L = L_{original} + \lambda \sum_{i=1}^{n}\sum_{j=1}^{m} \log P(W_{i,j}),$$

wherein in the formula, $L_{original}$ represents an original loss; and λ represents a regularization coefficient, n represents the total number of samples corresponding to the random-projected data; and m represents the total number of the bioinformatics features; and evaluating a second uncertainty of the uncertainties corresponding to the integrated prediction result by using a Monte Carlo method to perform approximate estimation, comprising: using a low-rank matrix decomposition to approximate a weight matrix W, which is expressed by the following formula:

$$W \approx U\sum V^T,$$

wherein in the formula, U, Σ, $V^T$ represent low-rank approximate representations of the weight matrix W; U represents a left vector matrix, a column vector of the U is an orthogonal basis of the weight matrix W; Σ represents a diagonal matrix, elements on a diagonal of the diagonal matrix are singular values and arranged in a descending order, and the singular values are non-zero root-mean-square eigenvalues of the weight matrix W; and $V^T$ represents a transpose matrix of a right vector, a row vector of the $V^T$ is another orthogonal basis of the weight matrix W;

step 5, performing personalized medical advice on a patient based on the integrated prediction result, the interpretability analysis, and the uncertainties corresponding to the integrated prediction result, thereby obtaining a gene candidate list corresponding to target diseases of the patient based on the personalized medical advice, wherein the gene candidate list provides candidate genes of the patient; and step 6, extracting clinical information of the patient from a medical database, integrating the clinical information with the candidate genes of the patient to construct an archive containing the candidate genes and the clinical information, generating a target treatment advice based on data of the archive, and performing clinical treatment on the patient based on the treatment advice to facilitate curing the patient.

2. The genome-wide prediction method based on deep learning according to claim 1, wherein during the model construction, the step 2 further comprises the following steps:

constructing the gene interaction graph G and creating a graph structure for an interaction between the genes, specifically comprising:
step 2.1, data acquisition;
step 2.2, data preprocessing;
step 2.3, constructing the graph structure; and
step 2.4, graph attribute analysis.

3. The genome-wide prediction method based on deep learning according to claim 1, wherein the step 3 further comprises: performing the model training by using gradient descent in batch to find an optimal parameter to make the hybrid model have an optimal performance during prediction, thereby obtaining the trained model weight.

4. The genome-wide prediction method based on deep learning according to claim 3, wherein the step 3 further comprises:

adding a constraint term based on a knowledge graph into the optimal loss function to obtain the trained model weight constrained by the knowledge graph.

5. The genome-wide prediction method based on deep learning according to claim 4, wherein the step 3 further comprises:

adding a regularization layer after an output of each network layer of the hybrid model to obtain a regularized model weight; and analyzing the regularized model weight by using shapley additive explanations (SHAP) and local interpretable model-agnostic explanations (LIME) to obtain the trained model weight and an importance score or a local interpretation model corresponding to each of the bioinformatics features.

6. A genome-wide prediction method based on deep learning, comprising the following steps:
step 1,
obtaining genome-wide data;
performing data cleansing on the genome-wide data to obtain cleansed genome-wide data;
performing data sparsity processing on the cleansed genome-wide data to obtain sparsity-processed genome-wide data, comprising:
performing dimensionality reduction on the cleansed genome-wide data according to principal component analysis to obtain dimensionality-reduced data;
performing random projection based on compressed sensing on the dimensionality-reduced data to obtain random-projected data;
coding the random-projected data by using a sparse autoencoder; and
defining an optimal loss function by a formula as follows:

$$J(\theta) = \frac{1}{n}\sum_{i=1}^{n}\left(\|Y_i - Y'_i\| + \lambda\|W_{enc}\|_1 + \beta\sum_{j=1}^{s}KL(\rho\|\hat{\rho}_j)\right),$$

wherein in the formula, $J(\theta)$ represents the optimal loss function and comprises: a reconstruction error, an L1 regularization of a weight of the sparse autoencoder, and a kullback-leibler (KL) divergence; $\|Y_i-Y'_i\|^2$ represents the reconstruction error of the optimal loss function, $\lambda\|W_{enc}\|_1$ represents the L1 regularization of the weight of the sparse autoencoder of the optimal loss function, and $KL(\rho\|\hat{\rho}_j)$ represents the KL divergence of the optimal loss function; n represents a total number of samples corresponding to the random-projected data; $Y_i$ represents an $i_{th}$ sample of the random-projected data obtained by performing the random projection; $Y'_i$ represents a reconstruction result obtained through coding the $i^{th}$ sample by the sparse autoencoder; $\lambda$ represents a regularization parameter of the L1 regularization, $\lambda$ is configured to control a sparsity of the weight of the sparse autoencoder, and $\lambda$ is determined and adjusted based on a verification data set; $W_{enc}$ represents the weight of the sparse autoencoder; $\|W_{enc}\|_1$ is an L1 norm of the $W_{enc}$ and represents a sum of absolute values of elements in the $W_{enc}$; $\beta$ represents a control parameter, $\beta$ is configured to control an influence of the KL divergence on a total loss, and $\beta$ is determined and adjusted based on the verification data set; s represents a number of neurons, and is determined according to model design; $\rho$ is a preset sparsity parameter and represents an average activation degree of a hidden layer; $\hat{\rho}_j$ represents an average activation degree of a $j^{th}$ hidden unit of the hidden layer, and is calculated according to a model output based on a training data set; and $KL(\rho\|\hat{\rho}_j)$ represents the KL divergence, and is configured to measure a difference or a divergence between two probability distributions;

extracting bioinformatics features from the sparsity-processed genome-wide data, comprising:
defining a correlation mapping matrix;
introducing graph theory and topological data analysis into the correlation mapping matrix, and defining a gene interaction graph G and a laplacian matrix L of the gene interaction graph G to thereby construct a feature matrix expressed by the following formula:

$$X = SVD(L) \times \left(\sum_{i=1}^{N} a_i \cdot I_i\right),$$

wherein in the formula, SVD (L) represents a singular value decomposition of the laplacian matrix L of the gene interaction graph G; N represents a layer number of an interaction matrix $I_i$; $a_i$ at represents a weight of an interaction intensity, and is derived from experimental data of an experiment including a co-immunoprecipitation experiment; It represents the interaction matrix located at different layers; and X represents the feature matrix reflecting interaction relationships of genes; and constructing a structure-retention mapping matrix, which is expressed by the following formula:

$$M = \frac{d}{dt}\left(\int_0^1 p(t) \times (q(t) - \sqrt{r(t)})dt\right),$$

wherein in the formula, p(t) represents a changing relationship between an annotation of a gene function and a time t; q(t) represents a biological characteristic of a disease caused by a gene under the time t; and r(t) represents an uncertainty of the gene function at the time t;

step 2, performing model construction based on the sparsity-processed genome-wide data and the bioinformatics features to obtain a hybrid model;

step 3, performing model training, regularization, and interpretability enhancement on the hybrid model to obtain a trained model weight and an interpretability analysis corresponding to the trained model weight;

step 4, performing learning and uncertainty estimation based on the trained model weight and to-be-predicted genome-wide data on the hybrid model to obtain an integrated prediction result and uncertainties corresponding to the integrated prediction result;

wherein the performing uncertainty estimation specifically comprises:

converting the trained model weight into a probability distribution, which is expressed as follows:

$$P(W_{i,j} | D) = \frac{P(D | W_{i,j})P(W_{i,j})}{P(D)},$$

wherein in the formula, $P(W_{i,j}|D)$ represents a posterior probability distribution of the trained model weight between an $i^{th}$ neuron of the neurons and a $j^{th}$ neuron of the neurons under the to-be-predicted genome-wide data D; $P(D|W_{i,j})$ represents a probability corresponding to the to-be-predicted genome-wide data D being observed under the trained model weight; $P(W_{i,j})$ represents a prior probability distribution of the trained model weight between the $i^{th}$ neuron and the $j^{th}$ neuron; and P(D) represents a marginal probability of the to-be-predicted genome-wide data D, and is a constant;

introducing a binary neural network, and evaluating a first uncertainty of the uncertainties corresponding to the integrated prediction result by using a weight distribution of the binary neural network, which is expressed as follows:

$$Y_{sample,k} = \sum_{i=1}^{n}\sum_{j=1}^{m} W_{sample,i,j} X_{i,j,k},$$

wherein in the formula, $Y_{sample,k}$ represents an output obtained from a $k^{th}$ sampling of the binary neural network; $W_{sample,i,j}$ represents a sampling result obtained through the $k^{th}$ sampling performed in the posterior probability distribution of the trained model weight between the $i^{th}$ neuron and the $j^{th}$ neuron; n represents the total number of samples corresponding to the random-projected data; m represents a total number of the bioinformatics features; and $X_{i,j,k}$ represents a sampling result obtained through the $k^{th}$ sampling of the $i^{th}$ neuron and the $j^{th}$ neuron;

regularizing the prior probability distribution of the trained model weight between the $i^{th}$ neuron and the $j^{th}$ neuron, which is expressed by the following formula:

$$L = L_{original} + \lambda \sum_{i=1}^{n}\sum_{j=1}^{m} \log P(W_{i,j}),$$

wherein in the formula, $L_{original}$ represents an original loss; and λ represents a regularization coefficient, n represents the total number of samples corresponding to the random-projected data; and m represents the total number of the bioinformatics features; and evaluating a second uncertainty of the uncertainties corresponding to the integrated prediction result by using a Monte Carlo method to perform approximate estimation, comprising: using a low-rank matrix decomposition to approximate a weight matrix W, which is expressed by the following formula:

$$W \approx U\Sigma V^T,$$

wherein in the formula, U, Σ, $V^T$ represent low-rank approximate representations of the weight matrix W; U represents a left vector matrix, a column vector of the U is an orthogonal basis of the weight matrix W; Σ represents a diagonal matrix, elements on a diagonal of the diagonal matrix are singular values and arranged in a descending order, and the singular values are non-zero root-mean-square eigenvalues of the weight matrix W; and $V^T$ represents a transpose matrix of a right vector, a row vector of the $V^T$ is another orthogonal basis of the weight matrix W;

step 5, performing personalized medical advice on a patient based on the integrated prediction result, the interpretability analysis, and the uncertainties corresponding to the integrated prediction result, thereby obtaining a gene candidate list corresponding to target diseases of the patient based on the personalized medical advice, wherein the gene candidate list provides candidate genes of the patient; and step 6, extracting clinical information of the patient from a medical database, integrating the clinical information with the candidate genes of the patient to construct an archive containing the candidate genes and the clinical information, generating a target treatment advice based on data of the archive, and performing physical treatment on the patient based on the treatment advice to facilitate curing the patient.

* * * * *